(12) United States Patent
Nosil

(10) Patent No.: US 8,708,562 B1
(45) Date of Patent: Apr. 29, 2014

(54) PHANTOM SYSTEMS AND METHODS FOR DIAGNOSTIC X-RAY EQUIPMENT

(71) Applicant: Nosil DSC Innovations Inc, Langley (CA)

(72) Inventor: Josip Nosil, Langley, CA (US)

(73) Assignee: Nosil DSC Innovations, Inc. (CA)

( * ) Notice: Subject to any disclaimer, the term of this patent is extended or adjusted under 35 U.S.C. 154(b) by 0 days.

(21) Appl. No.: 13/786,285

(22) Filed: Mar. 5, 2013

(51) Int. Cl.
*G01D 18/00* (2006.01)

(52) U.S. Cl.
USPC .......................................................... 378/207

(58) Field of Classification Search
USPC .................................................. 378/18, 207
See application file for complete search history.

(56) References Cited

U.S. PATENT DOCUMENTS

| | | |
|---|---|---|
| 4,638,502 A | 1/1987 | Yaffe |
| 5,236,363 A | 8/1993 | Sandrik et al. |
| 5,335,260 A | 8/1994 | Arnold |
| 5,493,601 A | 2/1996 | Fivez et al. |
| 5,651,046 A * | 7/1997 | Floyd et al. ............... 378/207 |
| 5,841,835 A | 11/1998 | Aufrichtig et al. |
| 5,910,975 A * | 6/1999 | Floyd et al. ............... 378/207 |
| 6,231,231 B1 | 5/2001 | Farrokhnia et al. |
| 6,315,447 B1 | 11/2001 | Nord et al. |
| 6,409,383 B1 | 6/2002 | Wang et al. |
| 6,488,409 B1 | 12/2002 | Vafi et al. |
| 6,632,020 B2 | 10/2003 | Kaufhold et al. |
| 6,811,310 B2 | 11/2004 | Lang et al. |
| 6,905,245 B2 | 6/2005 | Cresens |
| 6,979,124 B2 | 12/2005 | Gerwin et al. |
| 6,997,610 B2 | 2/2006 | Heismann |
| 7,039,163 B2 | 5/2006 | Popescu et al. |

(Continued)

FOREIGN PATENT DOCUMENTS

| | | |
|---|---|---|
| CA | 2419483 A1 | 3/2002 |
| GB | 2449113 A | 11/2008 |
| WO | 2008124649 A1 | 11/2008 |
| WO | 2011029910 A1 | 3/2011 |

OTHER PUBLICATIONS

Conway et al., Medical Physics, "Beam quality independent attenuation phantom for estimating patient exposure from x-ray automatic exposure controlled chest examinations", 1984, 1 page, vol. 11, No. 6, Center for Devices and Radiological Health, Food and Drug Administration, Rockville, MD.

Servomaa et al., BIR Report 18: Technical and Physical Parameters for Quality Assurance in Medical Diagnostic Radiology, "Patient equivalent phantoms in chest radiography", 1989, 4 pages, British Institute of Radiology, London.

(Continued)

*Primary Examiner* — Courtney Thomas
(74) *Attorney, Agent, or Firm* — Michael R. Schacht; Schacht Law Office, Inc.

(57) ABSTRACT

A phantom assembly for testing x-ray equipment comprising at least one image plate made, at least one base plate, at least one first plate, at least one second plate, at least one third plate. A base material is selected such that a base plate, and a image plate yield a first transmitted energy spectrum that emulates a first reference energy spectrum. A first plate material is selected such that a first plate, an image plate, and a base plate yield a second transmitted energy spectrum that emulates a second reference energy spectrum. A second plate material is selected such that a second plate, an image plate, and a base plate, yield a first transmitted doserate that emulates a first reference doserate. A third plate material is selected such that a third plate, a base plate, and a first plate yield a second transmitted doserate that emulates a second reference doserate.

20 Claims, 16 Drawing Sheets

(56) References Cited

U.S. PATENT DOCUMENTS

| | | |
|---|---|---|
| 7,056,019 B1 | 6/2006 | Hanson et al. |
| 7,056,020 B2 | 6/2006 | Saunders et al. |
| 7,173,238 B2 | 2/2007 | Karasawa |
| 7,256,392 B2 | 8/2007 | Sendai et al. |
| 7,391,892 B2 | 6/2008 | Gerwin |
| 7,510,325 B2 | 3/2009 | Endo et al. |
| 7,545,964 B2 | 6/2009 | Lang et al. |
| 7,642,506 B2 | 1/2010 | Wang et al. |
| 7,728,285 B2 | 6/2010 | Suh et al. |
| 7,729,524 B2 | 6/2010 | Rogers et al. |
| 7,950,849 B2 | 5/2011 | Claus et al. |
| 8,000,441 B2 | 8/2011 | Lang et al. |
| 2002/0061502 A1 | 5/2002 | Persohn et al. |
| 2005/0077459 A1 | 4/2005 | Engler et al. |
| 2005/0123093 A1 | 6/2005 | Lawaczeck et al. |
| 2008/0219412 A1 | 9/2008 | Lang |

OTHER PUBLICATIONS

Leeds Test Objects Sales Specifications, "medical imaging phantoms", Nov. 16, 2010 12 pages, North Yorkshire, UK.
Scanditronix Wellhofer Product Catalogue, "Quality Assurance in Digital Radiology: Measuring Instruments and Test Devices Main Products", Aug. 2006, pp. 6, 8, Germany, TN, Sweden, China.
AAPM Report No. 6, "Instrumentation Requirements of Diagnostic Radiological Physicists", 1998, 16 pages, Medical Physics Publishing, USA.
Schueler et al., Presentation "Use of the R/F Accreditation Phantom for Fluoroscopic System Evaluation", Jun. 2001, 66 pages.
Wilson et al., American College of Radiology, "Radiography Fluoroscopic Phantom", Jun. 2001, 8 pages, Medical Physics Publishing, USA.

\* cited by examiner

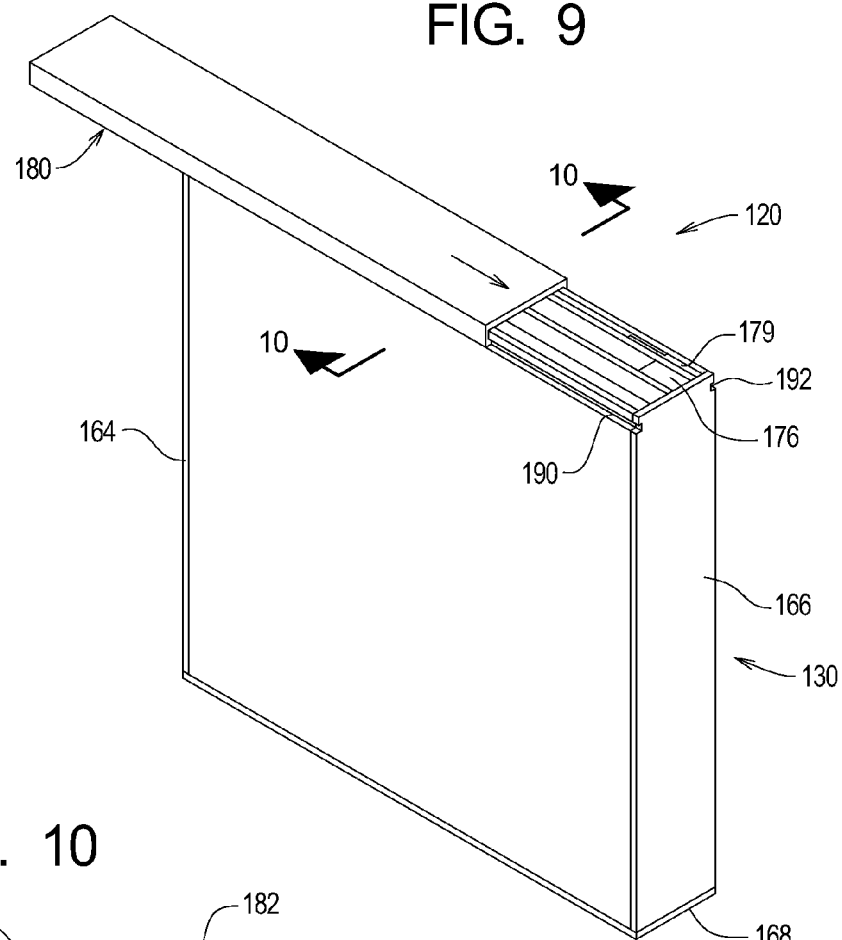
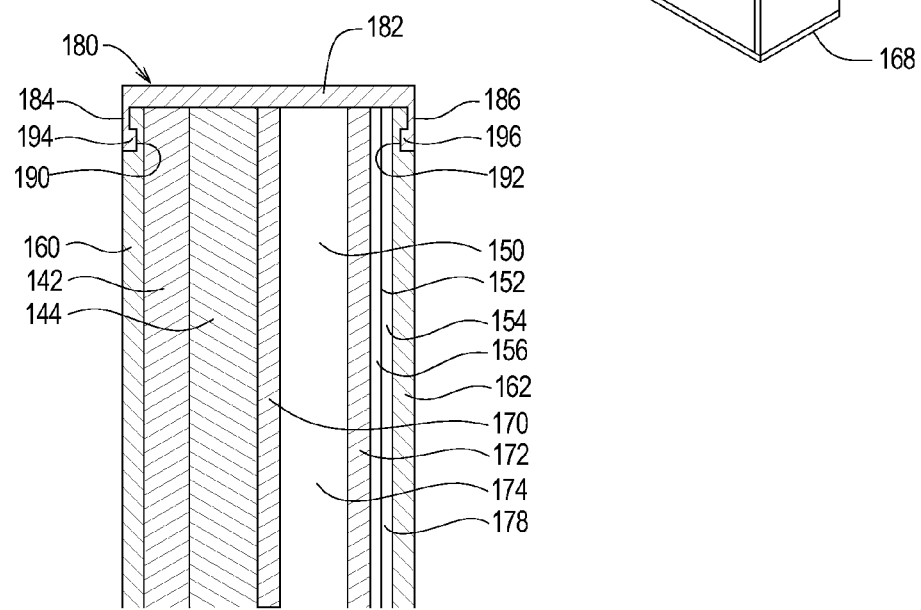

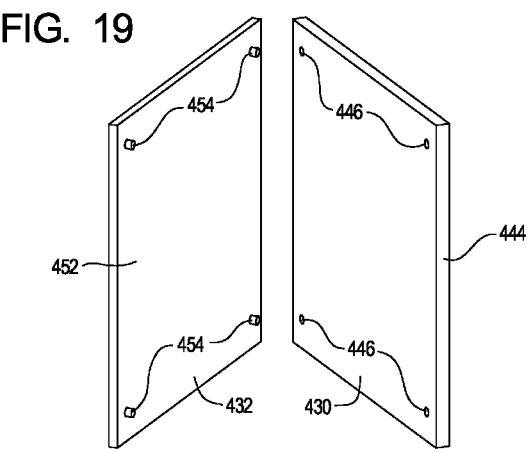
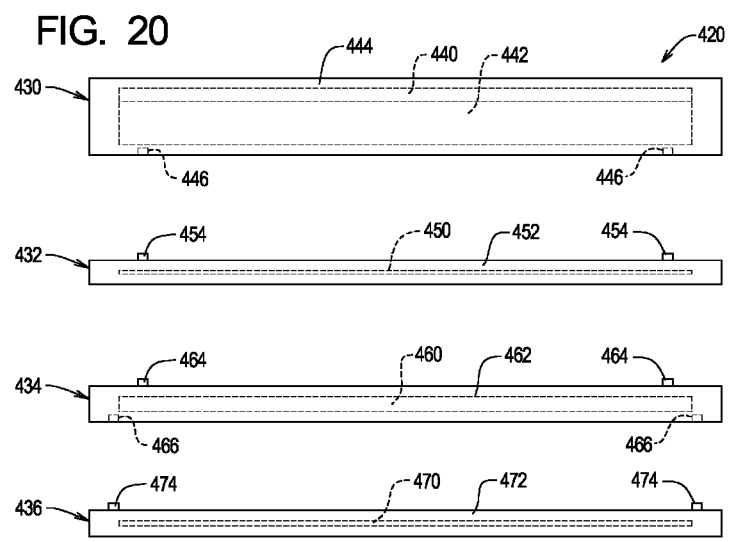

PHANTOM SYSTEMS AND METHODS FOR DIAGNOSTIC X-RAY EQUIPMENT

TECHNICAL FIELD

The present invention relates to the assessment of diagnostic x-ray equipment and, more particularly, to systems and methods for determining the quality of diagnostic x-ray equipment.

BACKGROUND

Quality Assurance (QA) of diagnostic x-ray equipment is necessary to ensure the production of high quality diagnostic information via x-ray images. Both initial acceptance testing and periodic routine examinations are part of quality assurance. The present invention has application to both radiographic and fluoroscopic commercial x-ray equipment.

The term "phantom" is typically applied to a device that is used for acceptance testing and routine ongoing testing of diagnostic x-ray equipment. In particular, a phantom is a device used to determine image quality and patient dose under clinical conditions. In addition to the phantom, certain other x-ray test equipment is necessary for Quality Assurance. Acceptance testing and the provision of a suitable ongoing testing routine are typically the responsibility of a qualified medical physicist. Periodic quality assurance using the prescribed testing routine is typically the responsibility of a designated and trained x-ray technologist.

A number of testing phantoms is available commercially: each has its recommended testing routine. The American College of Radiology has created a set of Accreditation Program Requirements and developed a phantom (the ACR phantom) that is commonly used according to those requirements for acceptance and ongoing testing of x-ray equipment. The ACR phantom produces information that allows the accurate assessment of the diagnostic quality of images produced by a medical x-ray unit.

The need thus exists for phantom systems and methods that allow the accurate assessment of the diagnostic quality of images produced by a medical x-ray unit but which are light, have a small form factor, and are convenient to use.

SUMMARY

The present invention may be embodied as a phantom assembly for testing x-ray equipment comprising at least one image plate made of at least one image plate material, at least one base plate made of at least one base material, at least one first plate made of at least one first plate material, at least one second plate made of at least one second plate material, at least one third plate made of at least one third plate material. The at least one base material is selected, sized, and dimensioned such that one base plate, in combination with one image plate, yields a first transmitted energy spectrum that emulates a first reference energy spectrum. The at least one first plate material is selected, sized, and dimensioned such that one first plate, in combination with one image plate and one base plate, yields a second transmitted energy spectrum that emulates a second reference energy spectrum. The at least one second plate material is selected, sized, and dimensioned such that one second plate, in combination with one image plate and one base plate, yields a first transmitted doserate that emulates a first reference doserate. The at least one third plate material is selected, sized, and dimensioned such that one third plate, in combination with one image plate,

[column 2]

one base plate, and one first plate yields a second transmitted doserate that emulates a second reference doserate.

The present invention may also be embodied as a method of testing x-ray equipment comprising the following steps. At least one image plate made of at least one image plate material is provided. At least one base plate is formed by selecting, sizing, and dimensioning at least one base plate material such that one base plate, in combination with one image plate, yields a first transmitted energy spectrum that emulates a first reference energy spectrum associated with a human chest. At least one first plate is formed by selecting, sizing, and dimensioning at least one first plate material such that one first plate, in combination with one image plate and one base plate, yields a second transmitted energy spectrum that emulates a second reference energy spectrum associated with a human abdomen. At least one second plate is formed by selecting, sizing, and dimensioning at least one second plate material such that one second plate, in combination with one image plate and one base plate, yields a first transmitted doserate that emulates a first reference doserate associated with a human chest. At least one third plate is formed by selecting, sizing, and dimensioning at least one third plate material such that one third plate, in combination with one image plate, one base plate, and one first plate yields a second transmitted doserate that emulates a second reference doserate associated with a human abdomen.

The present invention may also be embodied as a phantom assembly for testing x-ray equipment comprising a base assembly and first, second, and third plate assemblies. The base assembly comprises a base housing, an image plate made of at least one image plate material, at least one base plate made of at least one base material, and a base mounting portion. The first plate assembly comprises a first plate housing, a first plate made of at least one first plate material, a primary second housing mounting portion, and a secondary second housing mounting portion. The second plate assembly comprising a second plate housing, a second plate made of at least one second plate material, and a third housing mounting portion. The third plate assembly comprises a third plate housing, a third plate made of at least one third plate material, and a fourth housing mounting portion. The at least one base material is selected, sized, and dimensioned such that the base plate, in combination with the image plate, yields a first transmitted energy spectrum that emulates a first reference energy spectrum associated with a human chest. The at least one first plate material is selected, sized, and dimensioned such that the first plate, in combination with the image plate and the base plate, yields a second transmitted energy spectrum that emulates a second reference energy spectrum associated with a human abdomen. The at least one second plate material is selected, sized, and dimensioned such that the second plate, in combination with the image plate and the base plate, yields a first transmitted doserate that emulates a first reference doserate associated with a human chest. The at least one third plate material is selected, sized, and dimensioned such that the third plate, in combination with the image plate, the base plate, and the first plate yields a second transmitted doserate that emulates a second reference doserate associated with a human abdomen. The base mounting portion and the primary second housing mounting portion are configured to allow the first plate housing to be detachably attached to the base housing. The secondary second housing mounting portion and the third housing mounting portion are configured to allow the second plate housing to be detachably attached to the base housing. The base mounting portion and the fourth housing mounting portion are configured to allow the third plate housing to be detachably attached to the base housing.

BRIEF DESCRIPTION OF THE DRAWINGS

FIG. 9 is a perspective view of a second example base assembly of a second example phantom system of the present invention;

FIG. 10 is a section view taken along lines 10-10 in FIG. 9;

FIG. 19 is a perspective view depicting a portion of a fifth example phantom system of the present invention;

FIG. 20 is a plan view illustrating the fifth example phantom system of the present invention;

DETAILED DESCRIPTION

A phantom system constructed in accordance with, and embodying, the principles of the present invention may be embodied in a number of ways with certain parts common to the different embodiments. A number of examples of embodiments of phantom systems of the present invention will be presented below, followed by general explanations of the use of these phantom systems.

Additionally, the example phantoms of the present invention as described herein have application to both radiographic and fluoroscopic x-ray equipment. For the most part, the present invention has been discussed herein in the context of radiographic equipment for simplicity, but it should be understood that any reference to radiographic equipment may also refer to fluoroscopic equipment, and vice versa.

I. First Example Phantom System

Figure 1:
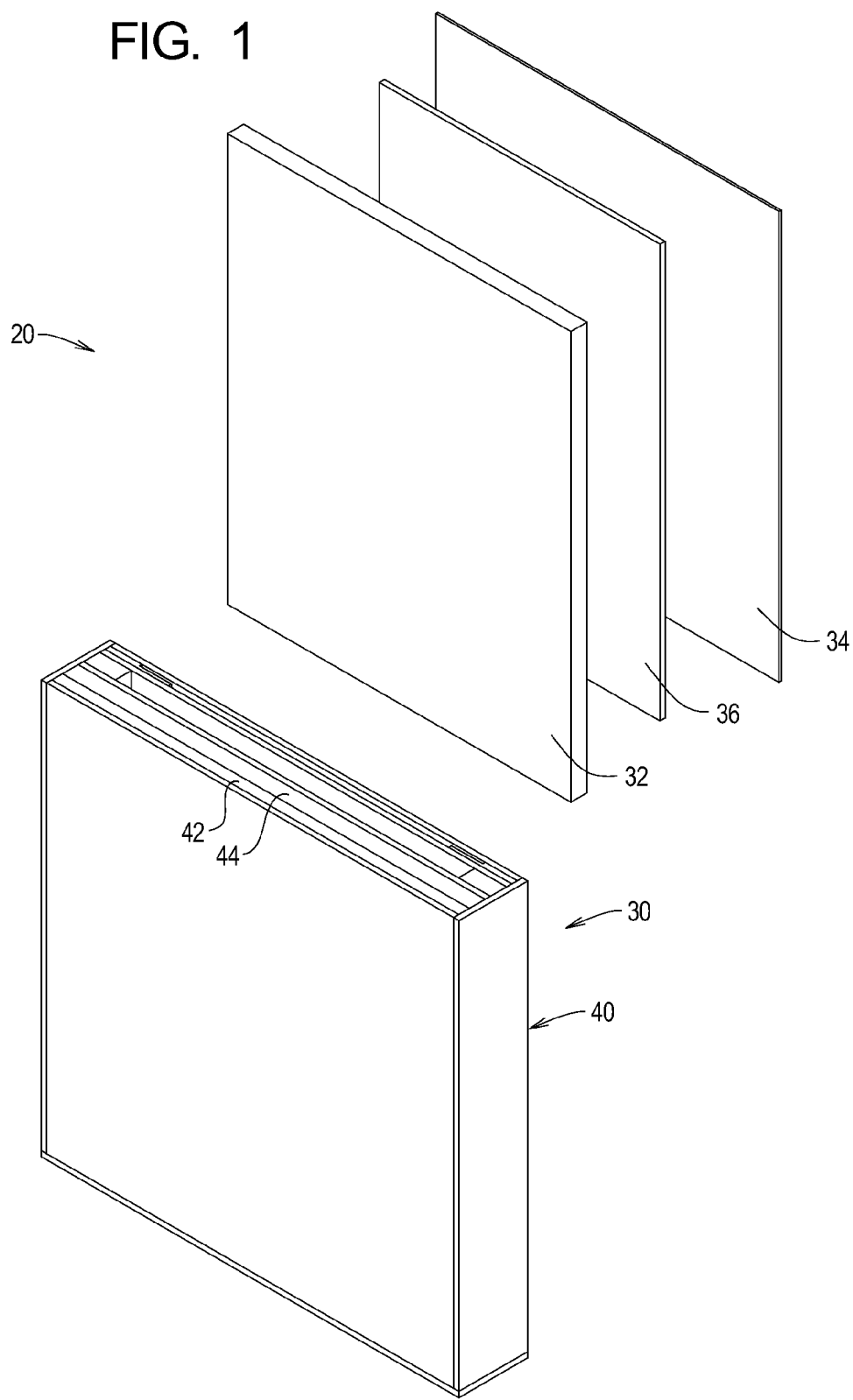
FIG. 1 is an exploded, perspective view of a first example phantom system of the present invention.

Referring initially to FIG. 1 of the drawing, a first example phantom system 20 is depicted therein. The first example phantom system 20 comprises a base assembly 30, a first plate 32, a second plate 34, and a third plate 36. The example base assembly 30 comprises a housing assembly 40, an image plate 42, and a base plate 44. The example image plate 42 and base plate 44 are integrally formed with the example housing assembly 40, but it may be possible to construct the base assembly 30 such that the image plate 42 and/or base plate 44 are detachably attached from the housing assembly 40.

Figure 2:
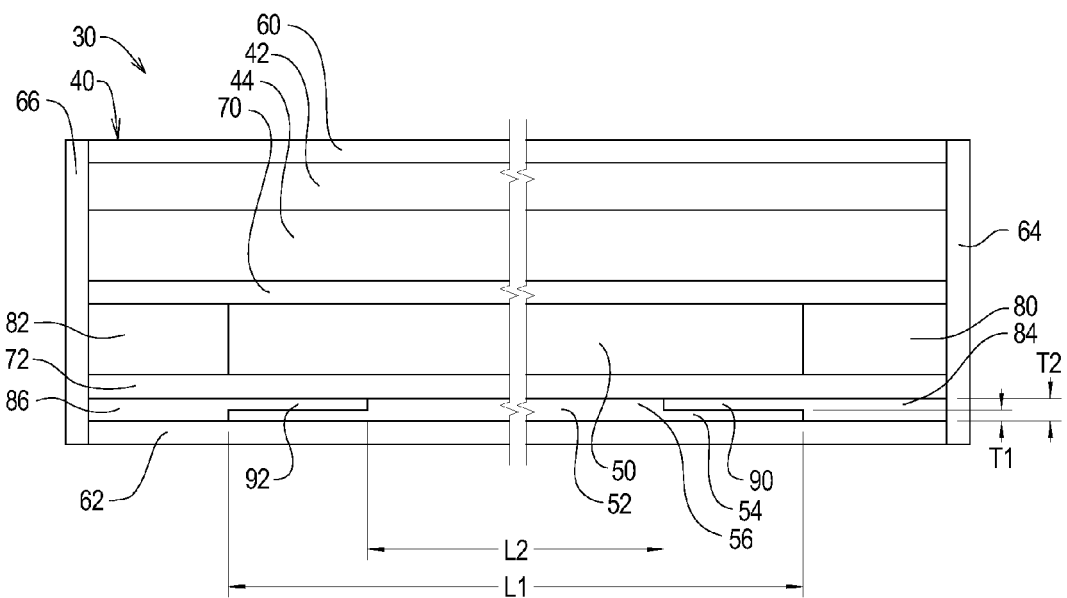
FIG. 2 is a partial plan view illustrating the first example phantom system in a first configuration.

As perhaps best shown in FIG. 2 of the drawing, the example base assembly 30 defines a first cavity 50 and a second cavity 52. The example second cavity 52 further defines a first portion 54 and a second portion 56. In particular, the first portion 54 of the second cavity 52 has a thickness T1 and a length L1. The second portion 56 of the second cavity 52 has a thickness T2 and a length L2. The first cavity portion 54 is thus wider and thinner than the second cavity portion 56.

The first example phantom system 20 is configured to operate in first, second, third, and fourth configurations. In the first configuration (best shown in FIG. 2), the base assembly 30 is used without any of the first, second, or third plates 32, 34, or 36, and the first and second cavities 50 and 52 are empty. The first example phantom system 20 in the first configuration is used to perform a chest image quality test.

Figure 3:
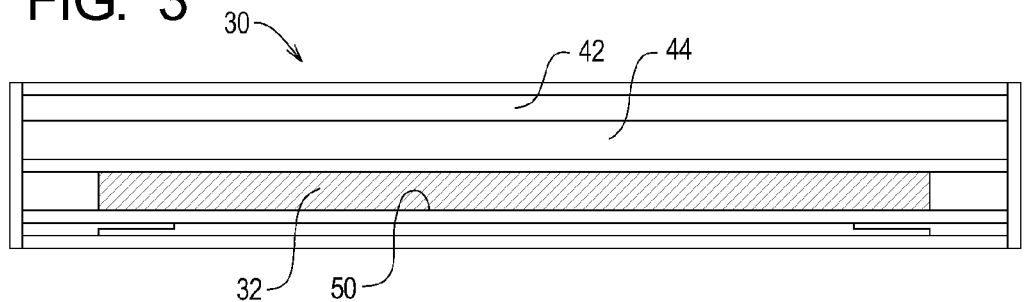
FIGS. 3, 4, and 5 are plan views similar to FIG. 2 illustrating the first example phantom system in a second, third, and fourth configurations.

In the second configuration (shown in FIG. 3), the base assembly 30 is used in conjunction with the first plate 32. In particular, the first plate 32 is inserted into the first cavity 50. The first example phantom system 20 in the second configuration is used to perform an abdomen image quality test.

Figure 4:
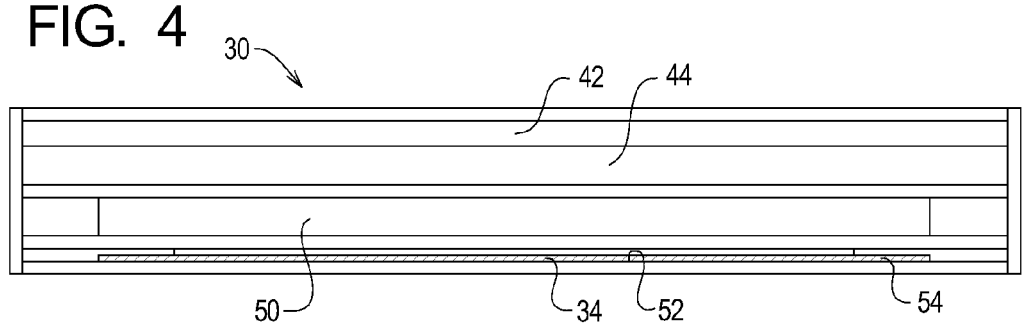

In the third configuration (shown in FIG. 4), the base assembly 30 is used in conjunction with the second plate 34. In particular, the second plate 34 is inserted into the first portion 54 of the second cavity 52. The second plate 34 is wider and thinner than the third plate 36. As discussed above, the first cavity portion 54 is similarly wider and thinner than the second cavity portion 56. Accordingly, only one of the second and third plates 34 and 36 may be inserted into the second cavity 52 at a time. The first example phantom system 20 in the third configuration is used to perform a chest doserate test.

Figure 5:
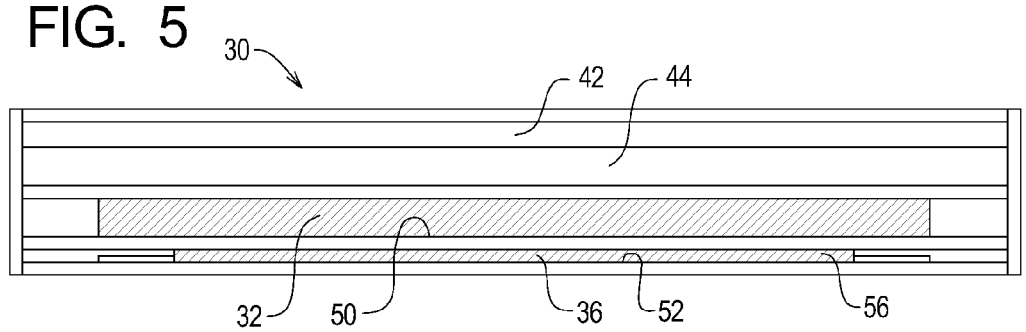

In the fourth configuration (shown in FIG. 5), the base assembly 30 is used in conjunction with the first plate 32 and the third plate 36. In particular, the first plate 32 is inserted into the first cavity 50 and the third plate 36 is inserted into the second portion 56 of the second cavity 52. Again, only one of the second and third plates 34 and 36 may be inserted into the second cavity 52 at a time. The first example phantom system 20 in the fourth configuration is used to perform an abdomen dose or doserate test.

Figure 6:
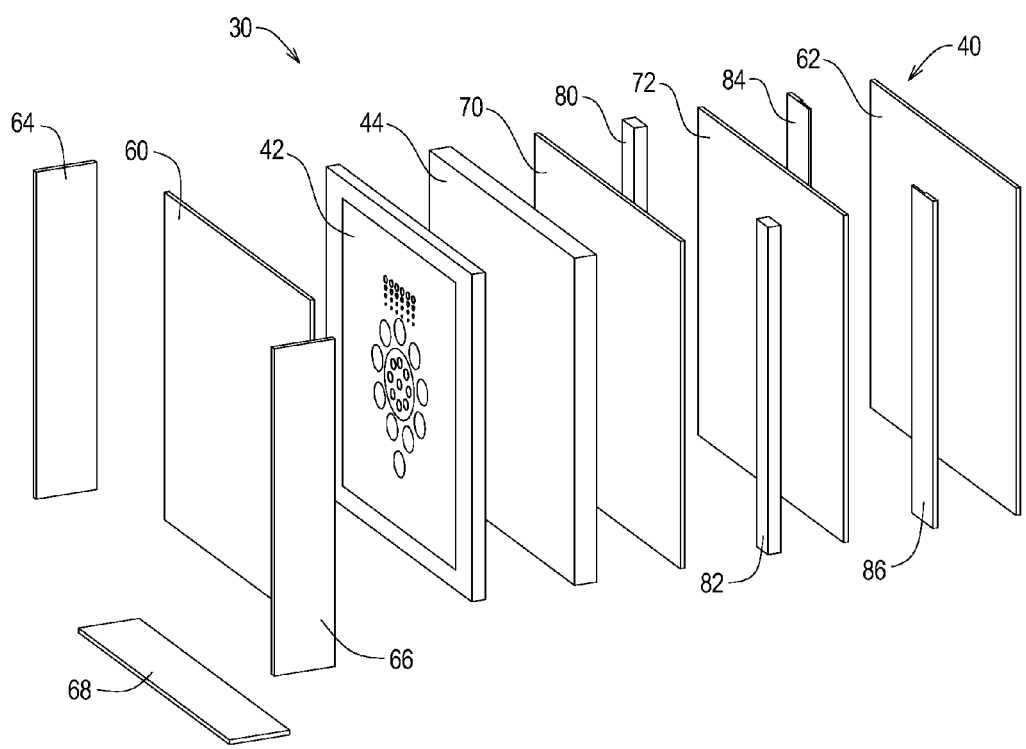
FIG. 6 is an exploded view of the base assembly of the first example phantom system.

FIGS. 2 and 6 of the drawing illustrates that the example housing assembly 40 of the example base assembly 30 comprises a first face cover sheet 60, a second face cover sheet 62, a first side cover sheet 64, a second side cover sheet 66, and an end cover sheet 68. FIGS. 2 and 6 further show that the example housing assembly 40 comprises a first spacer sheet 70, a second spacer sheet 72, a first spacer bar 80, a second spacer bar 82, a third spacer bar 84, and a fourth spacer bar 86. The third spacer bar 84 defines a first shoulder portion 90, while the fourth spacer bar 86 defines a second shoulder portion 92.

In the example base assembly 30, the image plate 42 is arranged between the first face cover sheet 60 and the base plate 44. In turn, the base plate 44 is arranged between the image plate 42 and the first spacer sheet 70. The first and second spacer bars 80 and 82 are arranged between the first and second spacer sheets 70 and 72 to define the first cavity 50. The third and fourth spacer bars 84 and 86 are arranged between the second spacer sheet 72 and the second face cover sheet 62 to define the second cavity 50. The first and second shoulder portions 90 and 92 of the third and fourth spacer bars 84 and 86 function to define the first and second cavity portions 54 and 56 of the second cavity 52.

The first and second side cover sheets 64 and 66 and the end cover sheet 68 are arranged to cover edges of the image plate 42 and base plate 44, face cover sheets 60 and 62, spacer sheets 70 and 72, and spacer bars 80, 82, 84, and 86. In the first example base assembly 30, adhesives are used to adhere the various plates, sheets, and spacer bars together.

The example first example phantom system 20 comprises an image plate 42, a base plate 44, a first plate 32, a second plate 34, and a third plate 36. Although the first example phantom system 20 comprises three plates, the advantages of the present invention may be realized using as few as one or two plates, and it may be possible to incorporate additional plates for additional test scenarios. Further, while the example image plate 42 and example base plate 44 are integrally formed with the housing assembly 40, one or both of the image plate 42 and base plate 44 may be removed from the housing assembly 40 as generally described above.

Figure 7:
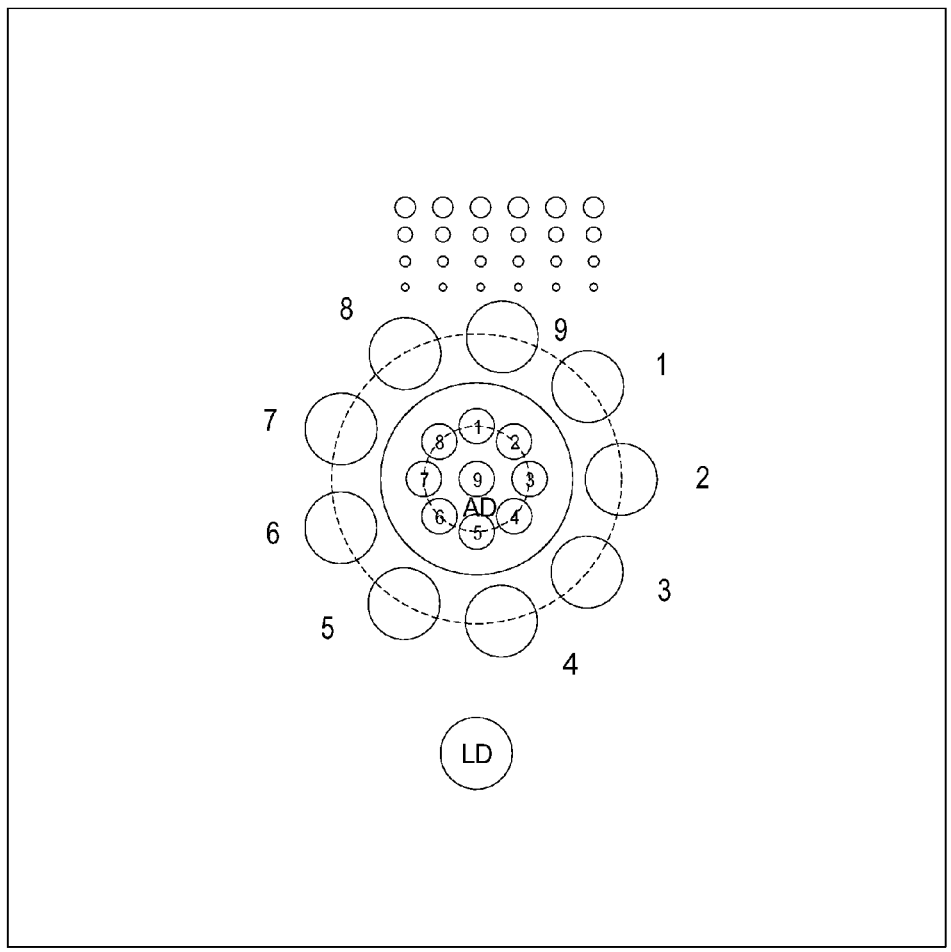
FIG. 7 is a plan view of a first image plate that may be used by a phantom system of the present invention.

The example image plate 42 is a conventional ACR image plate and contains structures that produce images that allow the image quality of the unit under test to be evaluated. The example image plate 42 comprises a 9.5 mm thick slab of Polymethylmethacrylate-Acrylic (PMMA) and image quality structures configured to result in an image that allows the evaluation of image quality characteristics such as high contrast resolution, low contrast resolution, low contrast details, and dynamic range (latitude). Details of a first example image plate 42 are shown in FIGS. 6 and 7.

The example image plate 42 allows high contrast image resolution to be evaluated from images representing 1.9 cm diameter copper mesh structures embedded in the PMMA slab at a depth of 5 mm. The mesh structures are formed in a range of mesh sizes. As one example, the mesh structures may range in size from 0.5 lp/mm to 3.2 lp/mm in nine steps. In the example image plate 42, the wires in the mesh structures are aligned at 45° to the cathode/anode direction. With the ACR image plate, the copper mesh structures are positioned in order of the size of the mesh and decreases in size in the clock-wise direction.

Low contrast resolution is evaluated from the images of nine holes in a 2 mm thick 1100 aluminum disc centered in the PMMA slab. In the example image plate 42, the holes have depths in the range of 0.1 mm to 1.7 mm. With the ACR image plate, the holes for determining low contrast resolution are positioned in order of the depth of the hole.

The contrast detail area may comprise four rows of six holes in the PMMA slab. In the example image plate 42, the holes in each row are of the same diameter, but the depths range from 0.3 mm to 1.5 mm in six steps, and the holes in the four rows range from 1.9 mm to 5.5 mm in diameter. With the ACR image plate, the holes for determining contrast detail are positioned in order of the depth of the hole.

The dynamic range may be evaluated from the image of an aluminum disk embedded in the PMMA plate. In the example image plate 42, the aluminum disk has a diameter of 19.5 mm and a thickness of 6.34 mm.

Figure 8:
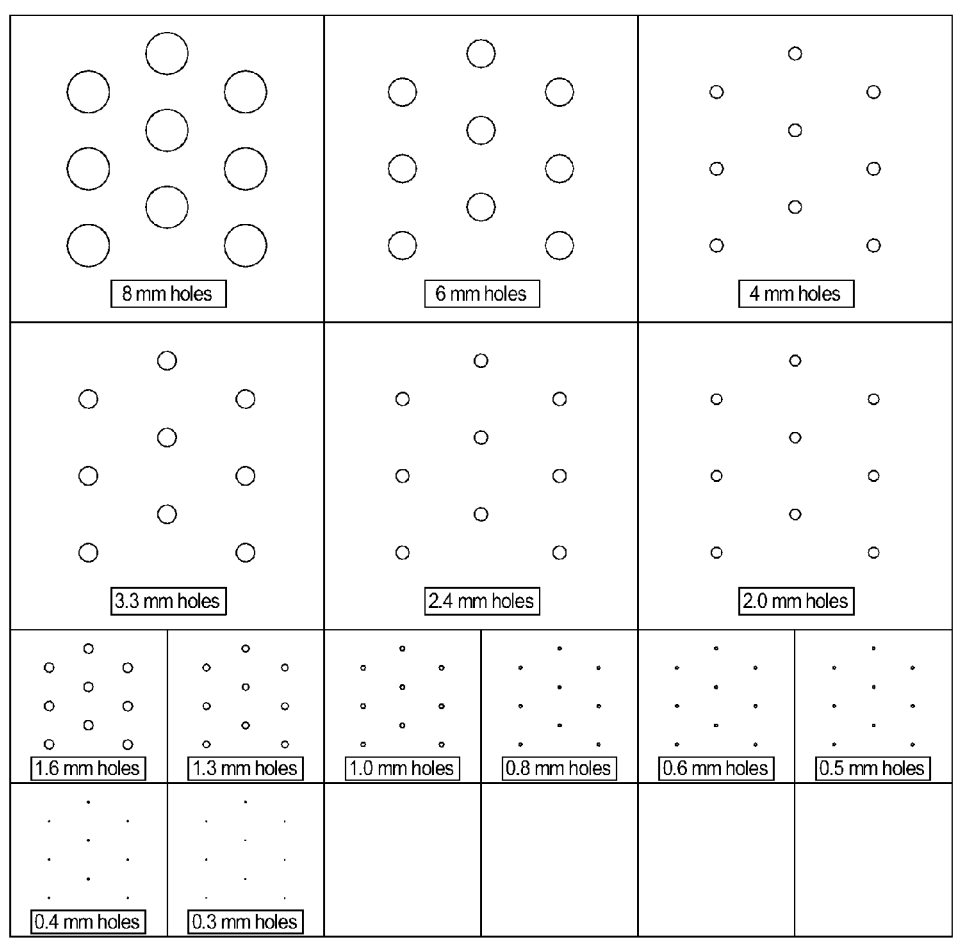
FIG. 8 is a plan view of a second image plate that may be used by a phantom system of the present invention.
Figure 11:
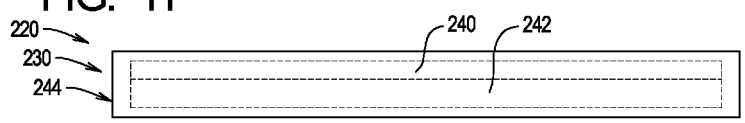
FIGS. 11-14 are plan views illustrating components that, when used together, form a third example phantom system of the present invention.
Figure 12:
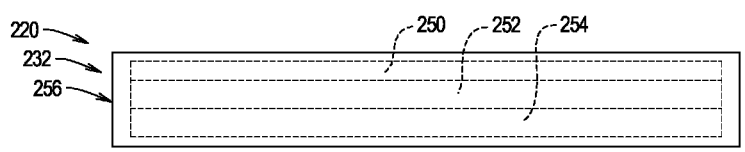
Figure 13:
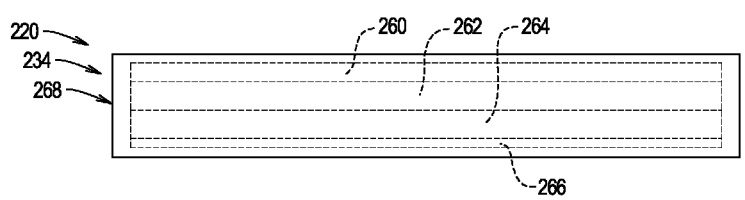

A second example image plate 46 that may be used instead of or in conjunction with the example image plate 42 is depicted in FIG. 8 of the drawing. The second example image plate 46 comprises structures that produce images that allow the image quality of the unit under test to be evaluated. The example image plate 42 comprises a slab of material such as 1100 aluminum and image quality structures configured to result in an image that allows the evaluation of image quality characteristics such as high contrast resolution, low contrast resolution, low contrast details, and dynamic range (latitude).

In particular, the example image plate 46 defines six large square aluminum square portions and twelve aluminum square portions arranged in the PMMA slab. Each of the large and small square portions contains nine holes all having the same diameter and different depths. The depths of the holes are randomly formed so that a technician must determine which hole is deeper by analysis. In addition, the spaces or positions (x, y position) between holes may be randomized. The random depths and spacing prevent an analyst, such as a radiologist, QC technologist, or service engineer, from reaching a predetermined conclusion on contrast resolution and contrast detail based on the sequential arrangement of the hole depths in the given square portions and not on a visual analysis of the actual image. To ensure randomness, a random number generator may be used to determine hole depths and placement. The example image plate 46 may be provided with mesh structures and other features to allow further analysis of the x-ray equipment forming the image.

The base plate 44 may be referred to as a base spectral plate and is formed of materials configured such that the energy spectrum transmitted through the base plate 44 is similar to that of the conventional ACR phantom. Or stated alternatively, the energy spectrum transmitted through the base plate should be similar or analogous to a first or chest reference energy spectrum translated through a typical human chest. The Applicant has determined that the energy spectrum transmitted by the ACR phantom, and thus the chest reference energy spectrum, may be duplicated or emulated using, as one example, an 18.7 mm thick assembly comprising 4 slabs of polyvinyl chloride (PVC) (totaling 12.7 mm thick) and two slabs of Acrylonitrile butadiene styrene (ABS) (totaling 6 mm thick). Other materials and/or combinations of materials that yield a transmitted energy spectrum similar to a chest reference energy spectrum may be used in place of the PVC and ABS slabs described herein.

The first plate 32 may be referred to as an abdomen attenuation plate. The example first plate 32 comprises two 3 mm thick slabs of 1100 aluminum and two 3 mm thick slabs of ABS. When the first plate 32 is used in combination with the image plate 42 and the base plate 44 (i.e., second configuration FIG. 3), the resulting total x-ray attenuation is similar to that of the ACR phantom configured to emulate the human abdomen and thereby yield a spectral response analogous to a second or abdomen reference energy spectrum corresponding to that of a typical human abdomen. The transmitted doserate is, however, considerably greater. Another material or combination of materials that, in combination with the image plate 42 and the base plate 44, yield a total x-ray attenuation similar to that of the ACR phantom configured to emulate an abdomen and thus yield a spectral response analogous to the abdomen reference energy spectrum associated with a typical human abdomen may be used in place of the aluminum and ABS slabs.

The second plate 34 may be referred to as a chest doserate plate. The example second insert is made of a single 0.8 mm thick plate of copper. When used in combination with the image plate 42 and the base plate 44 (i.e., third configuration FIG. 4), the resulting total x-ray doserate is similar to that transmitted by the typical human chest. Another material or combination of materials that, in combination with the image plate 42 and the base plate 44 yield a total x-ray doserate similar to that of the human chest may be used in place of the single copper plate.

The third plate 36 may be referred to as an abdomen doserate plate. The example third insert is made of a single 2.1 mm thick plate of copper. When used in combination with the image plate 42, the base plate 44, and the first plate 32 (i.e., fourth configuration FIG. 5), the resulting total x-ray doserate is similar to that transmitted by the human abdomen. Another material or combination of materials that, in combination with the image plate 42, the base plate 44, and first plate 32 yield a total x-ray doserate similar to that of the human abdomen may be used in place of the single copper plate.

To summarize then, the base plate 44 is made of at least one base material, the first plate 32 is made of at least one first plate material, the second plate 34 is made of at least one second plate material, and the third plate 36 is made of at least one third plate material. The at least one base material is selected, sized, and dimensioned such that the base plate 44, in combination with the image plate 42, yields a first transmitted energy spectrum that emulates a first reference energy spectrum associated with a human chest. The at least one first plate material is selected, sized, and dimensioned such that the first plate 32, in combination with the image plate 42 and the base plate 44, yields a second transmitted energy spectrum that emulates a second reference energy spectrum associated with a human abdomen. The at least one second plate material is selected, sized, and dimensioned such that the second plate 34, in combination with the image plate 42 and the base plate 44, yields a first transmitted doserate that emulates a first reference doserate associated with a human chest. The at least one third plate material is selected, sized, and dimensioned such that the third plate 36, in combination with the image plate 42, the base plate 44, and the first plate 32 yields a second transmitted doserate that emulates a second reference doserate associated with a human abdomen.

In addition, the form factor of the first example phantom system 20 can be 25 cm by 25 cm in area and 4.6 cm in total thickness. With this form factor and the materials forming the base assembly 30 and plates 32, 34, and 36 as described above, the total weight of all of the components of the first example phantom system 20 can be as little as approximately 7 lbs (3.2 kg).

II. Second Example Phantom System

Referring now to FIGS. 9 and 10 of the drawing, a second example phantom system 120 is depicted therein. The second example phantom system 120 comprises a base assembly 130, a first plate, a second plate, and a third plate. The first, second, and third plates are not illustrated in FIGS. 9 and 10 but would be constructed and used in substantially the same manner as the first, second, and third plates 32, 34, and 36 described above. The example base assembly 130 comprises a housing assembly 140, an image plate 142 (not shown?), and a base plate 144.

The example housing assembly 140 defines a first cavity 150 and a second cavity 152. The example second cavity 152 further defines a first portion 154 and a second portion 156. As with the example cavity portions 54 and 56 described above, first cavity portion 154 is thus wider and thinner than the second cavity portion 152.

The second example phantom system 120 is configured to operate in first, second, third, and fourth configurations. In the first configuration, the base assembly 130 is used without any of the first, second, or third plates, and the first and second cavities 150 and 152 are empty. The first example phantom system 120 in the first configuration is used to perform a chest image quality test. In the second configuration, the base assembly 130 is used in conjunction with the first plate to perform an abdomen image quality test. In the third configuration, the base assembly 130 is used in conjunction with the second plate to perform a chest doserate test. In the fourth configuration, the base assembly 130 is used in conjunction with the first plate and the third plate to perform an abdomen dose or doserate test.

FIGS. 9 and 10 of the drawing illustrate that the example housing assembly 140 of the example base assembly 130 comprises a first face cover sheet 160, a second face cover sheet 162, a first side cover sheet 164, a second side cover sheet 166, and an end cover sheet 168. FIG. 6 further shows that the example housing assembly 140 comprises a first spacer sheet 170 and a second spacer sheet 172. First and third spacer bars 174 and 176 are visible in FIG. 10. Like the first example base assembly 30, the second example base assembly 130 comprises a second spacer bar 176 and a fourth spacer bar 179 visible in FIG. 9.

FIGS. 9 and 10 further illustrate that the second example housing assembly 130 further comprises a cover member 180. The example cover member 180 defines a cover portion 182, a first connecting portion 184, and a second connecting portion 186. Formed in the first and second face cover sheets 160 and 162 are first and second connecting grooves 190 and 192. First and second connecting projections 194 and 196 are formed on the first and second connecting portions 184 and 186, respectively. Further, the connecting grooves 190 and 192 and connecting projections 194 and 196 are complementary such that the grooves 190 and 192 receive the projections 194 and 196.

Accordingly, the cover member 180 may be detachably attached to the base assembly 130 by sliding the cover member 180 such that the connecting projections 194 and 196 are received by the connecting grooves 190 and 192. The cover member 180 inhibits access to and possible contamination of the first and second cavities 150 and 152.

Ideally, the second example housing assembly 130 comprising the cover member 180, the first plate, 132, second plate 134, and third plate 136 can easily be cleaned and sterilized (e.g., autoclaved) without damage.

III. Third Example Phantom System

Figure 14:
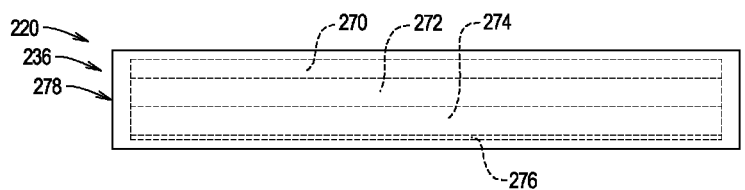
Figure 15:
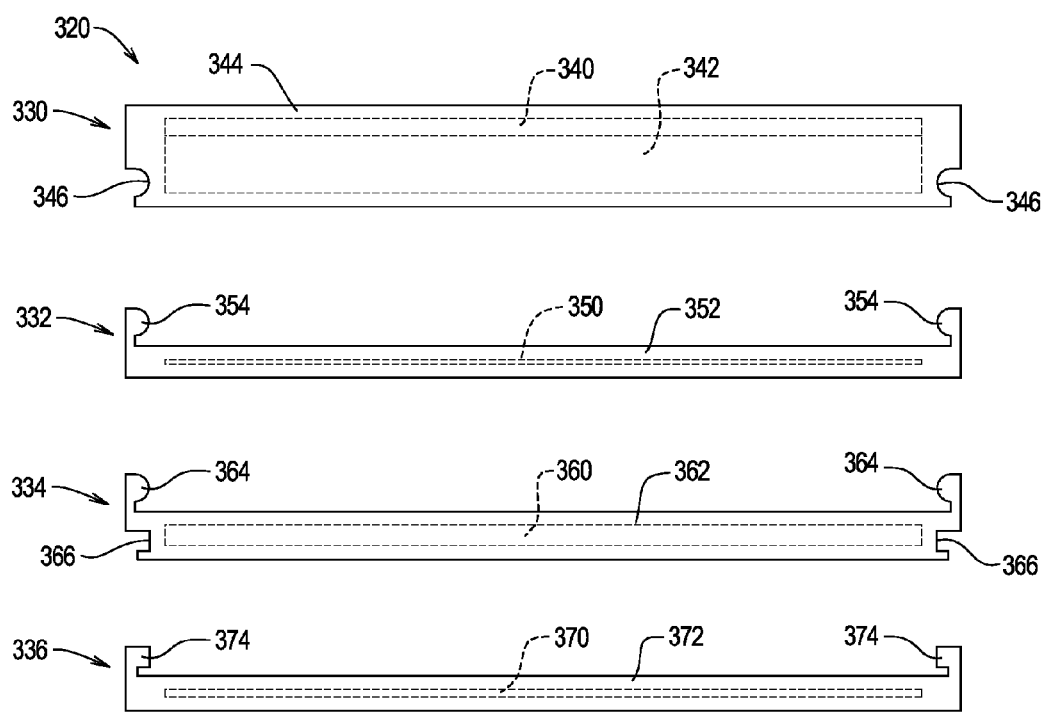
FIG. 15 is an exploded plan view of a fourth example phantom system of the present invention.
Figure 16:
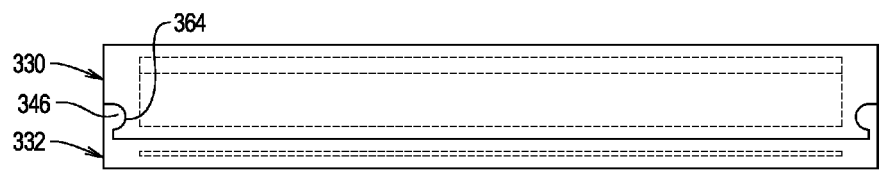
FIGS. 16-18 are plan views similar to FIG. 15 illustrating the fourth example phantom system in a second, third, and fourth configurations.
Figure 17:
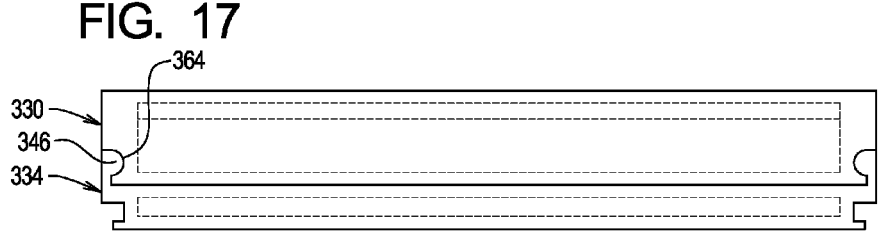
Figure 18:
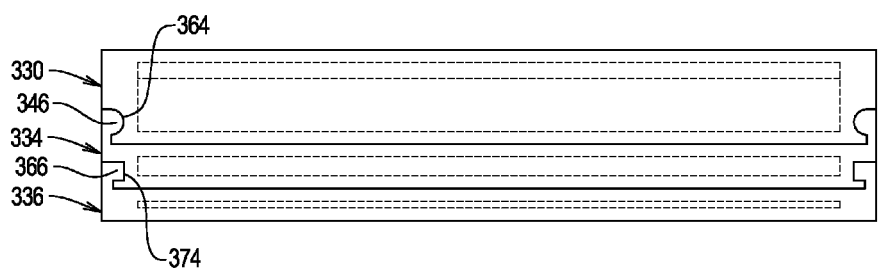

Referring now to FIGS. 11, 12, 13, and 14 of the drawing, depicted therein is a third example phantom system 220 of the present invention. The third example phantom system 220 comprises a first phantom assembly 230 (FIG. 11), a second phantom assembly 232 (FIG. 12), a third phantom assembly 234 (FIG. 13), and a fourth phantom assembly 236 (FIG. 14).

The first phantom assembly 230 (FIG. 11) comprises an image plate 240 and a first base plate 242 arranged within a first housing 244. The first base plate 242 may be integrally formed as part of the first housing 244. The second phantom assembly 232 (FIG. 12) comprises an image plate 250, a second base plate 252, a first plate 254, and a second housing 256. The second base plate 252 and first plate 254 may be integrally formed as part of the second housing 256. The third phantom assembly 234 (FIG. 13) comprises an image plate 260, a third base plate 262, a second plate 264, a third plate 266, and a third housing 268. The third base plate 262 and second plate 264 may be integrally formed as part of the third housing 268. The fourth phantom assembly 236 (FIG. 14) comprises an image plate 270, a fourth base plate 272, a fourth plate 274, a fifth plate 276, and a fourth housing 278. The fourth base plate 272 and fourth plate 274 may be integrally formed as part of the fourth housing 278.

The first, second, third, and fourth base plates 242, 252, 262, and 272 may be similar to the example base plate 42 described above. The first plate 254, second plate 264, and fourth plate 274 may be similar to the example first plate 32 described above. The example third plate 264 may be similar to the second plate 34 described above. The example fifth plate 276 may be similar to the third plate 36 described above.

The third example phantom system 220 is configured to operate in first, second, third, and fourth configurations. In the first configuration, the first phantom assembly 230 is used to perform a chest image quality test. In the second configuration, the second phantom assembly 232 is used to perform an abdomen image quality test. In the third configuration, the third phantom assembly 234 is used to perform a chest doserate test. In the fourth configuration, the fourth phantom assembly 236 is used to perform an abdomen dose or doserate test.

Ideally, the first, second, third, and fourth phantom assemblies 230, 232, 234, and 236 can easily be cleaned and sterilized (e.g., autoclaved) without damage.

IV. Fourth Example Phantom System

Referring now to FIGS. 15, 16, 17, and 18 of the drawing, depicted at 320 therein is a fourth example phantom system of the present invention. As perhaps best shown in FIG. 15, the fourth example phantom system 320 comprises a base assembly 330, a first plate assembly 332, a second plate assembly 334, and a third plate assembly 336.

The base assembly 330 comprises an image plate 340, a base plate 342, and a base housing 344. The base housing 344 defines base housing key slots 346. The base plate 342 may be integrally formed with the base housing 344. The first plate assembly 332 comprises a first plate 350 and a first plate housing 352. The first plate housing 352 defines first base housing key projections 354. The second plate assembly 334 comprises a second plate 360 and a second plate housing 362. The second plate housing 362 defines second base housing key projections 364 and extension housing key slots 366. The second plate 360 may be integrally formed with the second plate housing 362. The third plate assembly 336 comprises a third plate 370 and a third plate housing 372. Extension housing key projections 374 are formed on the third plate housing 372.

The base plate 342 may be similar to the example base plate 42 described above. The second plate 360 may be similar to the example first plate 32 described above. The example first plate 350 may be similar to the second plate 34 described above. The example third plate 370 may be similar to the third plate 36 described above.

The fourth example phantom system 320 is configured to operate in first, second, third, and fourth configurations. In the first configuration (FIG. 15), the base assembly 330 is used by itself to perform a chest image quality test.

In the second configuration (FIG. 16), the first plate assembly 332 is detachably attached to the base assembly 330 using the base housing key slots 346 and the first base housing key projections 354. In this second configuration, the first plate assembly 332 and base assembly 330 are used to perform a chest dose test.

In the third configuration (FIG. 17), the second plate assembly 334 is detachably attached to the base assembly 330 using the base housing key slots 346 and the second base housing key projections 364. The second plate assembly 334 and the base assembly 330 are used to perform a abdomen image quality test in the third configuration.

In the fourth configuration (FIG. 18), the second plate assembly 334 is detachably attached to the base assembly 330 using the base housing key slots 346 and the second base housing key projections 364, and the third plate assembly 336 is detachably attached to the second insert base assembly 334 using the extension housing key slots 366 and the extension housing key projections 374. In this fourth configuration, the base assembly 330, the second insert assembly 334, and the third insert assembly 336 are used to perform an abdomen dose or doserate test.

It should be noted that the relative positions of the various projections and slots may be exchanged without affecting the fundamental operation of the fourth example phantom system 320 as described below.

Ideally, the base assembly 330, first plate assembly 332, second plate assembly 334, and third plate assembly 336 can all be sterilized (e.g., autoclaved) without damage.

V. Fifth Example Phantom System

Referring now to FIGS. 19 and 20, depicted at 420 therein is a fifth example phantom system of the present invention. As shown in FIG. 20, the fifth example phantom system 420 comprises a base assembly 430, a first plate assembly 432, a second plate assembly 434, and a third plate assembly 436.

The base assembly 430 comprises an image plate 440, a base plate 442, and a base housing 444. The base housing 444 defines base housing key openings 446. The base plate 442 may be integrally formed with the base housing 444. The first plate assembly 432 comprises a first plate 450 and a first plate housing 452. The first plate housing 452 defines first base housing key projections 454. The second plate assembly 434 comprises a second plate 460 and a second plate housing 462. The second plate housing 462 defines second base housing key projections 464 and extension housing key openings 466. The second plate 460 may be integrally formed with the base housing 462. The third plate assembly 436 comprises a third plate 470 and a plate housing 472. Extension housing key projections 474 are formed on the third plate housing 472.

The base plate 442 may be similar to the example base plate 42 described above. The second plate 460 may be similar to the example first plate 32 described above. The example first plate 450 may be similar to the second plate 34 described above. The example third plate 470 may be similar to the third plate 36 described above.

The fourth example phantom system 420 is configured to operate in first, second, third, and fourth configurations. In the first configuration, the base assembly 430 is used by itself to perform a chest image quality test.

In the second configuration, the first plate assembly 432 is detachably attached to the base assembly 430 using the base housing key openings 446 and the first base housing key projections 454. In this second configuration, the first plate assembly 432 and base assembly 430 are used to perform chest/skin dose test.

In the third configuration, the second plate assembly 434 is detachably attached to the base assembly 430 using the base housing key openings 446 and the second base housing key projections 464. The second plate assembly 434 and the base assembly 430 are used to perform an abdomen image quality test in the third configuration.

In the fourth configuration, the second plate assembly 434 is detachably attached to the base assembly 430 using the base housing key openings 446 and the second base housing key projections 464, and the third plate assembly 436 is detachably attached to the second insert base assembly 434 using the extension housing key openings 466 and the extension housing key projections 474. In this fourth configuration, the base assembly 430, the second insert assembly 434, and the third insert assembly 436 are used to perform an abdomen dose or doserate test.

It should be noted that the relative positions of the various projections and openings may be exchanged without affecting the fundamental operation of the fourth example phantom system 320 as described below.

Ideally, the base assembly 430, first plate assembly 432, second plate assembly 434, and third plate assembly 436 can all be sterilized (e.g., autoclaved) without damage.

VI. Example Test Environments

Figure 21A:
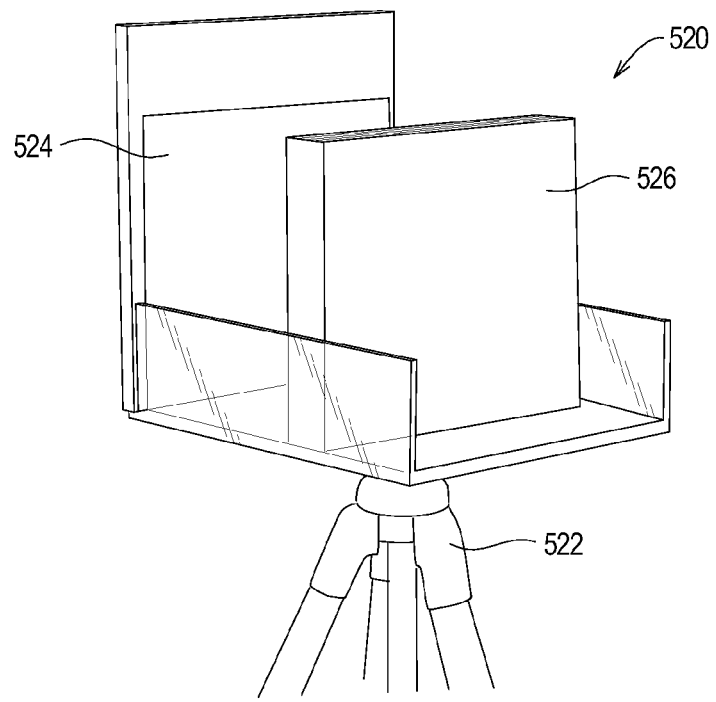
FIGS. 21A and 21B are perspective views illustrating the use of any of the example phantom systems described above in an image quality chest test configuration and a doserate chest test configuration.
Figure 21B:
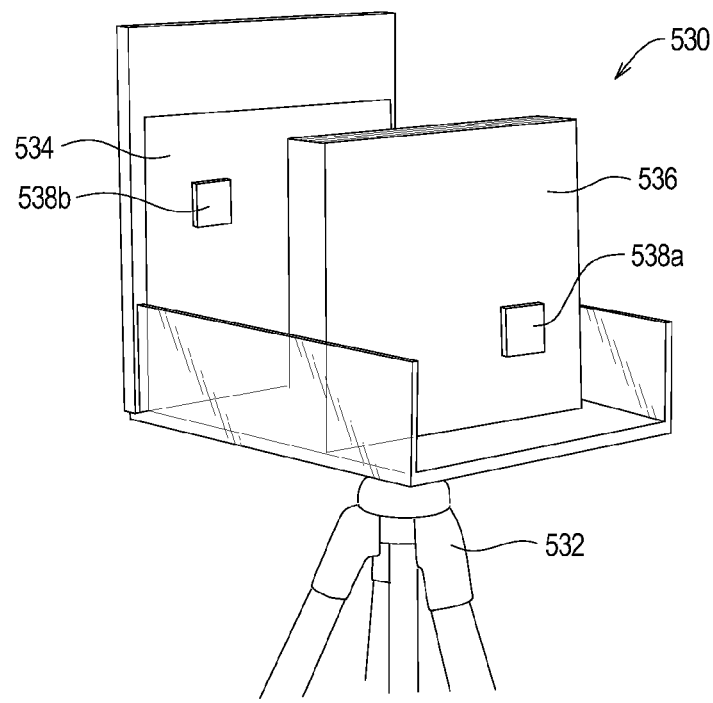
Figure 22A:
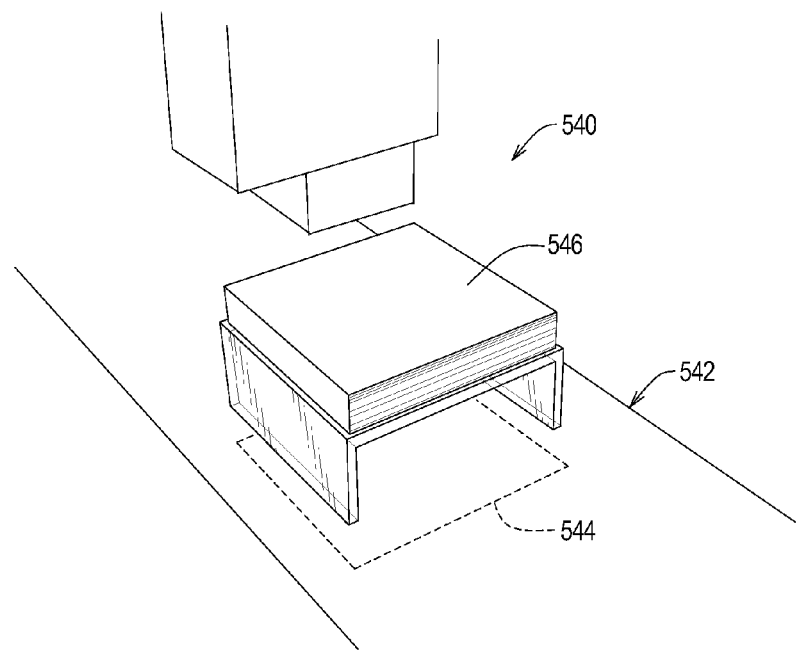
FIGS. 22A and 22B are perspective views illustrating the use of any of the example phantom systems described above in an image quality abdomen test configuration and a doserate abdomen test configuration.
Figure 22B:
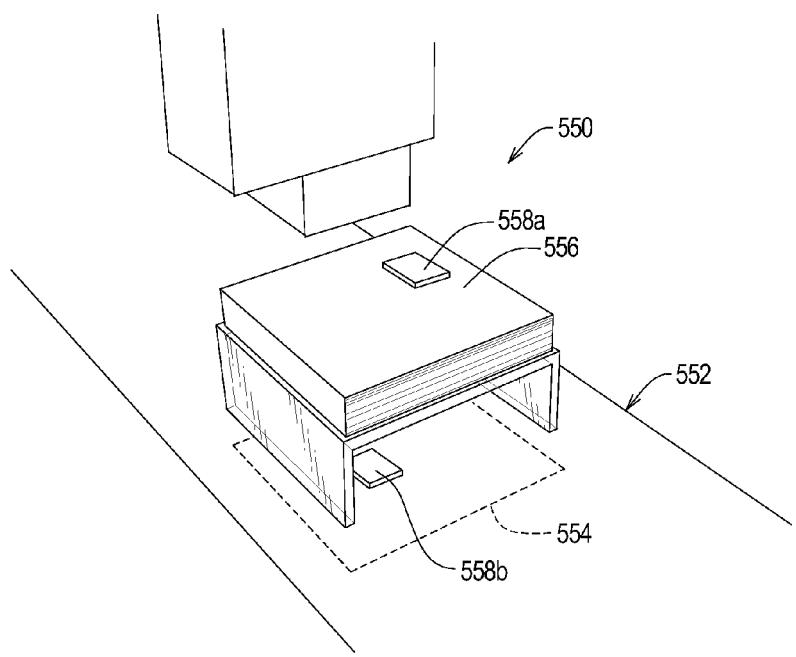

Most radiographic units can be used in two configurations: with a horizontal beam directed at a wall bucky for routine chest x-rays as shown in FIGS. 21A and 21B, and with a vertical beam directed at a table bucky for examinations of the abdomen of the supine or prone patient as shown in FIGS. 22A and 22B.

FIG. 21A depicts a first example use environment 520 in which a support structure 522 supports an x-ray image detection system 524 (e.g., film, computer radiography (CR), and digital radiography (DR)) and a phantom assembly 526 for use with a horizontal beam. FIG. 21B depicts a second example use environment 530 in which a support structure 532 supports an x-ray image detection system 534 (e.g., film, computer radiography (CR), and digital radiography (DR)) and a phantom assembly 536 for use with a horizontal beam. The second example use environment 530 further employs first and second dose detectors 538a (chest skin dose measurement detector) and 538b (imaging detector input dose detector) for measuring dosage on either side of the phantom assembly 536 in the direction of travel of the horizontal beam.

FIG. 22A depicts a third example use environment 540 in which a support structure or table 542 supports an x-ray image detection system 544 (e.g., film, computer radiography (CR), and digital radiography (DR)) and a phantom assembly 546 for use with a vertical beam. FIG. 22B depicts a fourth example use environment 550 in which a support structure 552 supports an x-ray image detection system 554 (e.g., film, computer radiography (CR), and digital radiography (DR)) and a phantom assembly 556 for use with a vertical beam. The fourth example use environment 550 further employs first and second dose detectors 558a (abdomen skin dose or doserate) and 558b (imaging detector input dose or doserate detector) for measuring dosage on either side of the phantom assembly 556 in the direction of travel of the vertical beam.

In both alignments, the same x-ray tube, energized by the same generator, may be employed. The amount of inherent and added filtration in the beam is fixed, but the kVp, mAs per exposure, and focal spot to detector distance are at the discretion of the operator.

The testing procedures for both radiographic and fluoroscopic units involve the use of a phantom assembly, together with the following additional equipment:

1. Any available commercial instrument capable of measuring exposure (in μSv), effective kVp and exposure time. Alternatively, separate instruments may be used to perform these functions;
2. An alignment test tool, incorporating radio-opaque indices to display field size and position on a film receptor;
3. A chest stand for chest exposures (FIG. 1) (incorporating a lead beam-defining plate);
4. A number of 1 or 2 mm thick 1100 aluminum plates with which to determine the HVL of the beam, and a number of Cu plates for uniformity and dosimetry assessments. An abdomen stand replaces the chest stand for abdomen-related tests with aluminum, copper and lead plates;
5. A radiation survey meter sensitive enough to measure scattered radiation;
6. A fluoroscopic RMI alignment test tool (or equivalent) used with copper plates and abdomen stand; and
7. Software for data entry, calculations and report generation.

Using a phantom system of the present invention and the additional equipment described in this Section VI, the following tests in radiography may be performed on x-ray generators according to standard testing protocols: Alignment Test; Kolovoltage kVp Test; Half Value Layer Test; Timer Accuracy and Reproducibility Test; Linearity Test; Wall Bucky Chest Image Quality Test; Patient Chest Dose Determination and Reproducibility Test; Radiation Survey near a chest unit; Table Bucky Abdomen Image Quality Test; Patient Abdomen Dose Determination and Reproducibility Test; Radiation Dose to Operator for Abdomen Protocol Test.

Similarly, the following tests in fluoroscopy may be performed using a phantom system of the present invention and the appropriate additional equipment as defined in this Section VI: Fluoroscopy Alignment Test; Fluoroscopy Image Quality; Patient Doserate in Fluoroscopy.

VII. Plate Material Selection

A description of the selection of materials and material dimensions of a phantom system constructed in accordance with the principles of the present invention will now be described.

1. Effect of the Variables Involved in X-Ray Generation

In this subsection, mAs correction factors for abdomen and chest examinations which make the air kerma emitted by the example phantom of the present invention equal that by the ACR phantom are determined.

First, the effect of the variables involved in x-ray generation, using the Spectrum abdomen (80 kVp) and chest (120 kVp) phantoms as models will be determined a compared to those involving the ACR phantom.

After measuring the Half-Value Layer (HVL) of the emitted beam, Reilly's method is used to determine the effective equivalent of aluminum in the x-ray beam as it emerges from the tube head. In the SR78 calculations, this amount of aluminum is added to that included in each phantom (ACR and Spectrum). Then, for four chosen HVL's at the two kVp's (80 ABD and 120 CHEST), the effective kVp, 1st HVL and Air Kerma in uGy/mAs are evaluated for the radiation emerging from the ACR and the example phantom of the present inventions. This allows for a comparison of the two in terms of the radiation transmitted by each.

The following Table 1 contains the results for the ACR Phantom for the following parameters: CHEST 120 kVp, 17 target, 0 ripple, 750 mm distance, 4.6 mm Al and 85.5 mm PMMA.

TABLE 1

| Measured HVL | Equivalent mm Al | Total Equiv Al | KeV | 1st HVL | uGy/mAs |
|---|---|---|---|---|---|
| 2.0 | 0.56 | 5.16 | 64.1 | 7.9 | 25.0 |
| 3.0 | 1.19 | 5.79 | 64.6 | 8.07 | 23.5 |
| 4.0 | 2.22 | 6.82 | 65.4 | 8.3 | 21.3 |
| 4.5 | 2.86 | 7.46 | 65.0 | 8.5 | 20.0 |
| 5.0 | 3.59 | 8.19 | 66.3 | 8.65 | 18.8 |

The following Table 2 contains the results for an example phantom assembly constructed in accordance with the principles of the present invention under the following parameters: CHEST 120 kVp, 17 degree target, 0 ripple 750 mm distance example phantom of the present invention, including 9.5 mm PMMA, 12.7 mm Bone (the nearest equivalent to PVC), 12.48 water (equivalent to 12 mm ABS), No Al.).

TABLE 2

| Measured HVL | Equivalent mm Al | Total Equiv Al | KeV | 1st HVL | uGy/mAs |
|---|---|---|---|---|---|
| 2.0 | 0.56 | 0.56 | 65.3 | 8.44 | 66.9 |
| 3.0 | 1.19 | 1.19 | 65.7 | 8.6 | 63.2 |
| 4.0 | 2.22 | 2.22 | 66.3 | 8.78 | 57.7 |
| 4.5 | 2.86 | 2.86 | 66.3 | 8.9 | 54.6 |
| 5.0 | 3.59 | 3.59 | 67.0 | 9.0 | 51.3 |

The following Table 3 contains the results for the ACR Phantom under the following parameters: ABDOMEN 80 kVp, 17 target, 0 ripple, 750 mm distance; ACR phantom, including 4.6 mm Al and 202.5 mm PMMA.

TABLE 3

| Measured HVL | Equivalent mm Al | Total Equiv Al | KeV | 1st HVL | uGy/mAs |
|---|---|---|---|---|---|
| 2.0 | 1.44 | 6.04 | 55.3 | 7.0 | 0.353 |
| 3.0 | 3.03 | 7.63 | 55.9 | 7.2 | 0.299 |
| 4.0 | 5.19 | 9.79 | 56.7 | 7.48 | 0.241 |
| 4.5 | 6.54 | 11.14 | 57.1 | 7.6 | 0.212 |

The following Table 4 contains the results for an example phantom assembly constructed in accordance with the principles of the present invention under the following parameters: ABDOMEN: 80 kVp, 17 degree target, 0 ripple, 750 mm distance example phantom of the present invention 9.5 mm PMMA, 12.7 mm Bone, 6.0 mm Al, 18.72 mm water (equiv to 18 mm ABS).

TABLE 4

| Measured HVL | Equivalent mm Al | Total Equiv Al | KeV | 1st HVL | uGy/mAs |
|---|---|---|---|---|---|
| 2.0 | 1.44 | 7.44 | 55.6 | 7.2 | 7.95 |
| 3.0 | 3.03 | 9.03 | 56.2 | 7.4 | 6.78 |
| 4.0 | 5.19 | 11.19 | 56.8 | 7.6 | 5.5 |
| 4.5 | 6.54 | 12.54 | 57.2 | 7.7 | 4.83 |
| 5.0 | 8.14 | 12.74 | 57.5 | 7.8 | 0.182 |

Comparing the results in Tables 1 and 2, it can be seen that, while the emitted spectra are nearly identical, the kerma/mAs ratio of Spectrum/ACR is approx 2.7 at 120 kVp. Therefore, in practice, we divide the mAs used with the ACR phantom by this factor to arrive at the value of the mAs to be used with the example phantom of the present invention.

Comparing the results in Tables 3 and 4, the spectra are again nearly the same, while the kerma/mAs ratio Spectrum/ACR is approx 22 at 80 kVp. Therefore, in practice, we divide the mAs used with the ACR phantom by this factor to arrive at the value of the mAs to be used with the example phantom of the present invention. If it is considered desirable to adjust the kerma output of the example phantom of the present invention at both 120 and 80 kVp to equal that of the ACR phantom, additional absorption may be added. This is examined in the following subsection.

2. Determination of Thickness of Copper Plates Forming Example Second and Third Insert Plates In this subsection, the thickness of copper that will reduce the air kerma emitted by the example phantom of the present invention to equal that emitted by the ACR phantom, using the same mAs setting, will be determined.

Having, as a preliminary step, measured the HVL of the bare beam, Reilly's method is used to evaluate the effective equivalent of aluminum in it. In using SR78, we then add this amount of filtration to that provided by each phantom (ACR and Spectrum). Then, for four chosen HVL's at the two kVp's (80 ABD and 120 CHEST) we evaluate the effective kVp, 1st HVL and uGy/mAs, as follows:

From Tables 1 and 2 above, the following Table 5 may be obtained:

TABLE 5

| Row | Measured HVL | Equivalent mm Al | Total equiv Al | KeV eff | 1$^{st}$ HVL | uGy/mAs |
|---|---|---|---|---|---|---|
| 1 | 2.0 | 0.559 | 0.559 | 65.3 | 8.46 | 66.9 |
| 2 |  |  | +0.8 Cu | 76.5 | 11.5 | 22.0 |
| 3 | 3.0 | 1.19 | 1.19 | 65.7 | 8.59 | 63.2 |
| 4 |  |  | +0.8 Cu | 76.6 | 11.5 | 22.0 |
| 5 | 4.0 | 2.22 | 2.22 | 66.3 | 8.8 | 57.7 |
| 6 |  |  | +0.8 Cu | 76.9 | 11.6 | 20.7 |
| 7 | 5.0 | 3.59 | 3.59 | 67.1 | 9.05 | 51.3 |
| 8 |  |  | +0.8 Cu | 77.3 | 11.7 | 19.0 |

The figures in rows 2, 4, 6, and 8 demonstrate that when 0.8 mm of Cu is used as part of the example phantom of the present invention, the emergent Air Kerma is reduced to that emitted by the ACR phantom. The keV and HVL go up however.

Recalling Tables 3 and 4 above, the following Table 6 may be obtained:

TABLE 6

| Row | Measured HVL | Equiv mm Al | Total Equiv Al | KeV eff | 1$^{st}$ HVL | uGy/mAs |
|---|---|---|---|---|---|---|
| 1 | 2.0 | 1.44 | 7.44 | 55.7 | 7.22 | 7.78 |
| 2 |  |  | +2.1 Cu | 66.3 | 10.3 | 0.321 |
| 3 | 3.0 | 3.03 | 9.03 | 56.2 | 7.40 | 6.6 |
| 5 |  |  | +2.1 Cu | 66.4 | 10.5 | 0.288 |
| 5 | 4.0 | 5.19 | 11.19 | 56.5 | 7.62 | 5.35 |
| 6 |  |  | +2.1 Cu | 66.5 | 10.3 | 0.248 |
| 7 | 4.5 | 6.54 | 12.54 | 57.2 | 7.74 | 4.71 |

When 2.1 mm Cu is used as part of the abdominal example phantom of the present invention the emergent Air Kerma will be the same as that of the ACR phantom, as shown by the numbers in rows 3, 5, and 7.

3. X-Ray Mass Attenuation Coefficients

A) Bone and Polyvinyl Chloride

Figure 23:
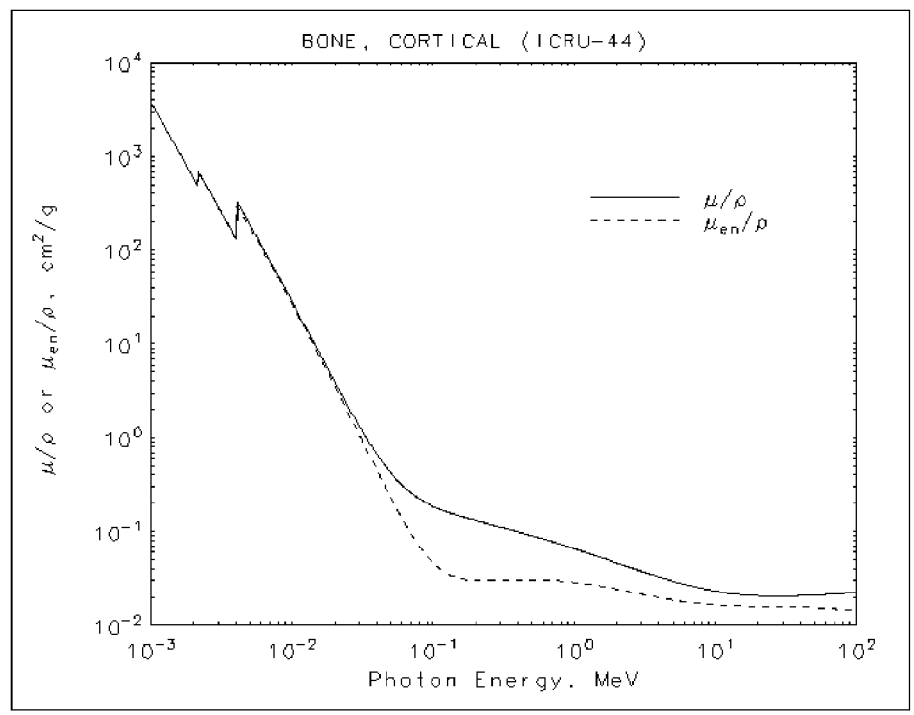
FIG. 23 is a first graph showing attenuation versus photon energy for bone.
Figure 24:
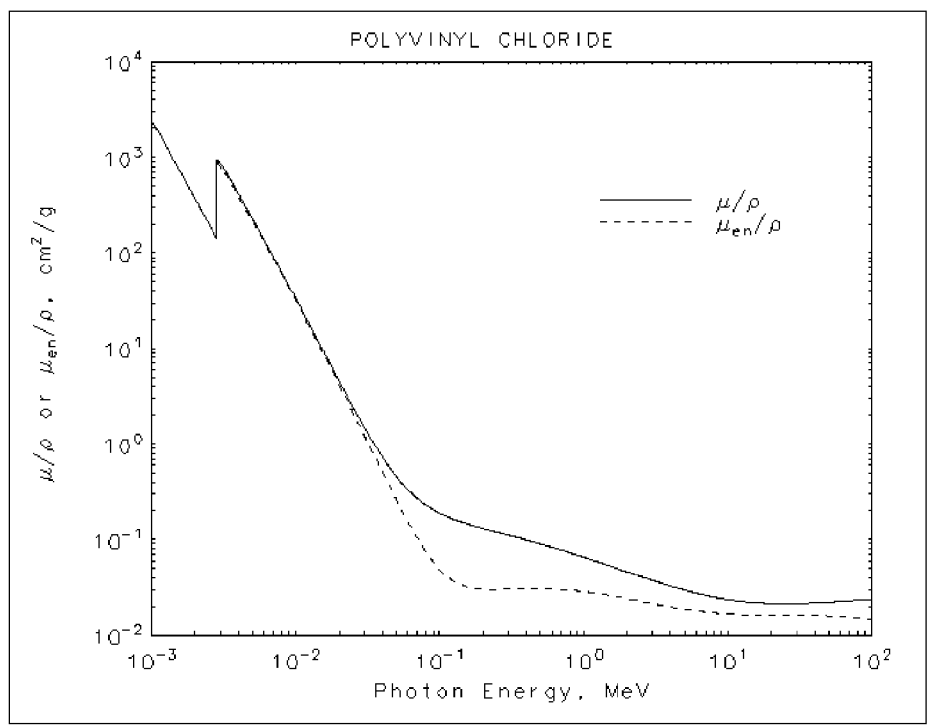
FIG. 24 is a second graph showing attenuation versus photon energy for PVC.

A comparison of FIGS. 23 and 24 shows attenuation versus photon energy in kV. The Applicant has determined that PVC is a close fit to the attenuation by bone and that PVC is an appropriate material that may be used as a replacement for or as a representative of bone in the phantom systems of the present invention.

B) Soft Tissue and PMMA

Figure 25:
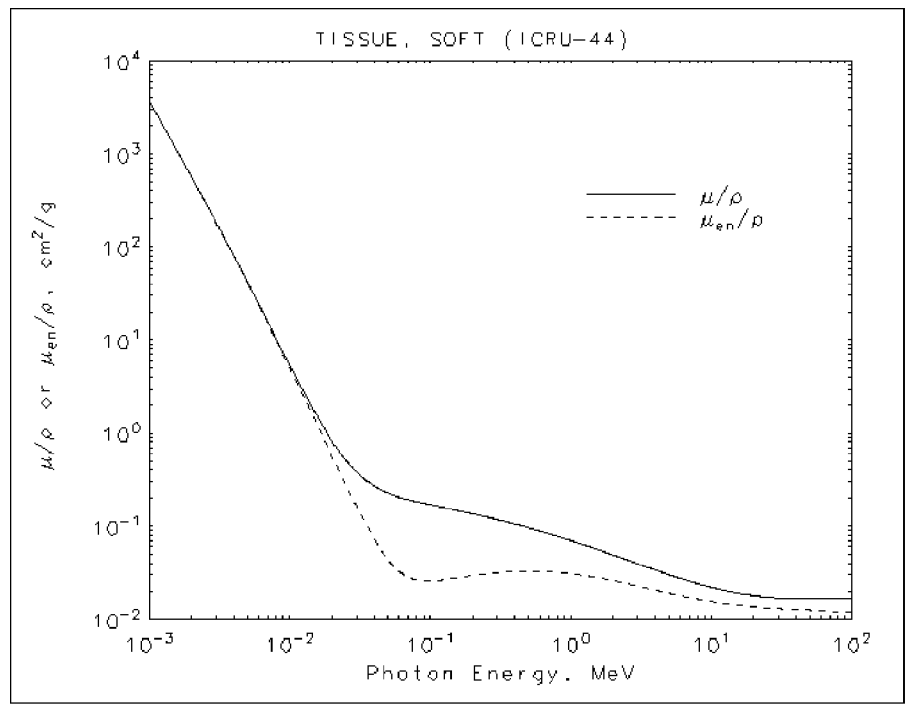
FIG. 25 is a third graph showing attenuation versus photon energy for soft tissue.
Figure 26:
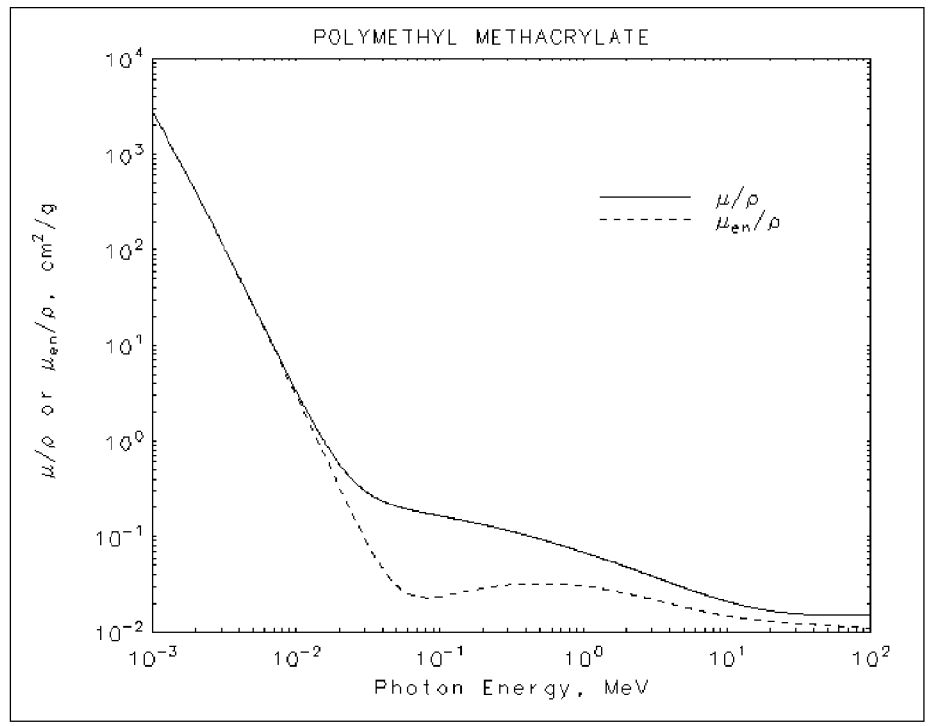
FIG. 26 is a fourth graph showing attenuation versus photon energy for PMMA.

As shown by a comparison of FIGS. 25 and 26, the Applicant has determined that the closest fit to attenuation by soft tissue is PMMA, so, correcting for density, PMMA is used as a tissue replacement in the example phantom of the present invention.

C) Material Constants and Composition Assumptions

The following Table 7 contains material constants and composition assumed in the present evaluations for compounds and mixtures. The compositions of various human tissues were taken from ICRU Report 44 (1989). Values are given for the mean ratio of atomic number-to-mass Z/A, the mean excitation energy I, and the density. Some density values are only nominal.

TABLE 7

X-Ray Mass Attenuation Coefficients

| Material | $\langle Z/A \rangle$ | I (eV) | Density (g/cm3) | Composition (Z: fraction by weight) | |
|---|---|---|---|---|---|
| Poly-methyl Methacrylate | 0.53937 | 74.0 | 1.190 | 1: 0.080541<br>6: 0.599846 | 8: 0.319613 |
| Water, Liquid | 0.55508 | 75.0 | 1.000 | 1: 0.111898 | 8: 0.888102 |
| Polystyrene | 0.53768 | 68.7 | 1.060 | 1: 0.077421 | 6: 0.922579 |
| Polyvinyl Chloride | 0.51201 | 108.2 | 1.406 | 1: 0.048382<br>6: 0.384361 | 17: 0.567257 |
| Bone, Cortical (ICRU-44) | 0.51478 | 112.0 | 1.920 | 1: 0.034000<br>6: 0.155000<br>7: 0.042000<br>8: 0.435000<br>11: 0.001000 | 12: 0.002000<br>15: 0.103000<br>16: 0.003000<br>20: 0.225000 |

VII. Third Example Image Plate

Figure 27:
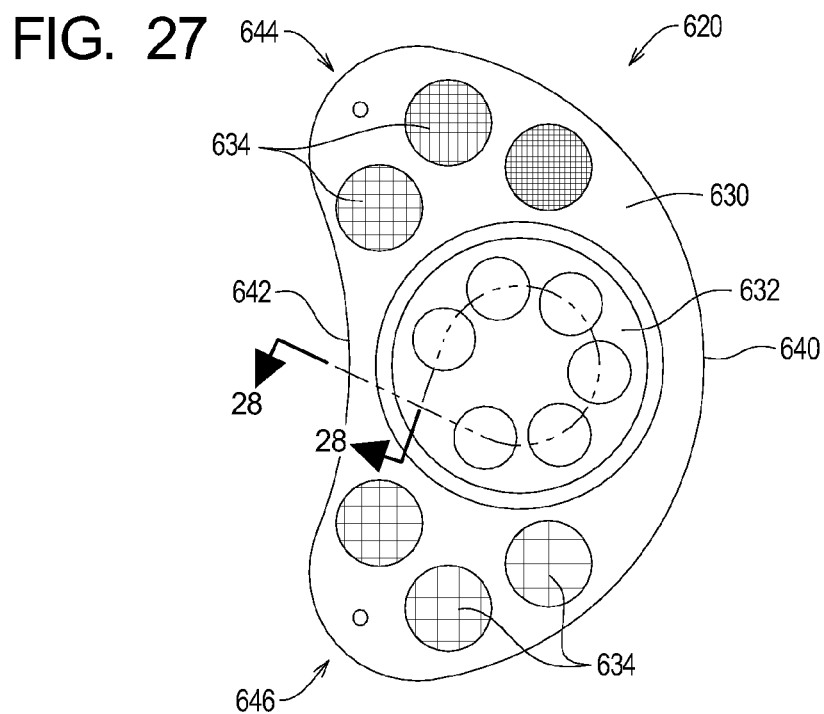
FIG. 27 is a plan view of a third example image plate of the present invention.
Figure 28:
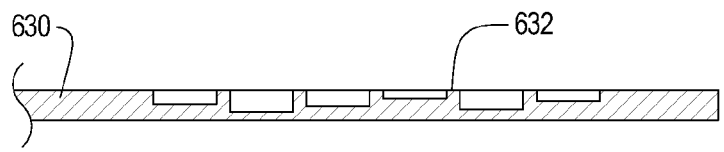
FIG. 28 is a section view taken along lines 25-25 in FIG. 24.
Figure 29:
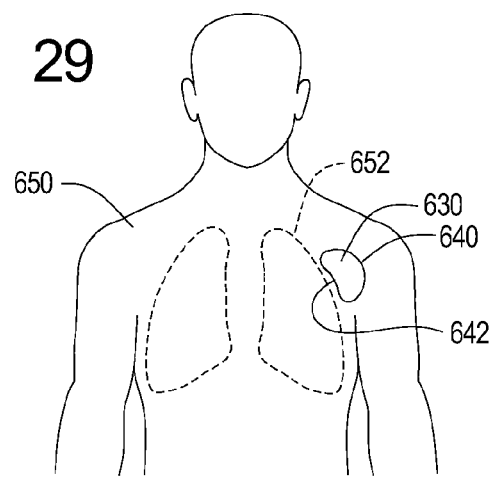
FIG. 29 is a front elevation view depicting the use of the third example image plate.

Referring now to FIGS. 27, 28, and 29, depicted therein is a third example image plate 620 constructed in accordance with, and embodying, the principles of the present invention. The third example image plate 620 comprises a plate body 630, an insert plate 632, and a plurality of mesh members 634. The plate body 630 is preferably made of PMMA, the mesh structures 634 are made of copper wire, and the insert plate 632 is preferably made of aluminum.

The example mesh structures 634 are 1.9 cm diameter copper mesh structures embedded in the PMMA slab at a depth of 5 mm that allow high contrast image resolution to be evaluated from images representing these structures 6344. The mesh structures are formed in a range of mesh sizes. As one example, the mesh structures may range in size from 0.5 lp/mm to 3.2 lp/mm in nine steps. In the example image plate 42, the wires in the mesh structures are aligned at 45° to the cathode/anode direction.

Low contrast resolution may be evaluated from the images of six holes in in the insert plate 632. In the example image plate 42, the holes have depths in the range of 0.1 mm to 1.7 mm and are randomly distributed along a circular line.

As shown in FIGS. 27 and 29, the plate body 630 defines a convex curved edge 640 and a concave curved edge 642 joined by end portions 644 and 646. The example plate body 630 is arranged on or near to a patient 650 such that the concave curved edge 642 avoids a lung location 652 of the patient. The plate body 630 is left in place during an x-ray process in which an image is made of the patient's lungs. The image formed by the plate 620 is thus associated with the patient and can be subsequently used to verify the accuracy of the image of the patient's lungs.

What is claimed is:

1. A phantom assembly for testing x-ray equipment comprising:
    at least one image plate made of at least one image plate material;
    at least one base plate made of at least one base material;
    at least one first plate made of at least one first plate material;
    at least one second plate made of at least one second plate material;
    at least one third plate made of at least one third plate material; wherein
    the at least one base material is selected, sized, and dimensioned such that one base plate, in combination with one image plate, yields a first transmitted energy spectrum that emulates a first reference energy spectrum;
    the at least one first plate material is selected, sized, and dimensioned such that one first plate, in combination with one image plate and one base plate, yields a second transmitted energy spectrum that emulates a second reference energy spectrum;
    the at least one second plate material is selected, sized, and dimensioned such that one second plate, in combination with one image plate and one base plate, yields a first transmitted doserate that emulates a first reference doserate; and
    the at least one third plate material is selected, sized, and dimensioned such that one third plate, in combination with one image plate, one base plate, and one first plate yields a second transmitted doserate that emulates a second reference doserate.

2. A phantom assembly as recited in claim 1, further comprising a housing for supporting one image plate, one base plate, and at least one of one first plate, one second plate, and one third plate.

3. A phantom assembly as recited in claim 2, in which the housing defines:
    a first slot adapted to receive the first plate; and
    a second slot defining a first portion sized and dimensioned to receive the second plate and a second portion sized and dimensioned to receive the third plate.

4. A phantom assembly as recited in claim 3, in which the at least one second plate, the at least one third plate, and second slot are sized and dimensioned such that the second slot receives only one of the first and second plates at a time.

5. A phantom assembly as recited in claim 3, further comprising a housing cover adapted to engage the housing to cover the first and second slots.

6. A phantom assembly as recited in claim 2, in which the housing is configured to operate in first, second, third, and fourth configurations, wherein:
    the housing combines one image plate and one base plate in the first configuration;

the housing combines one image plate, one base plate, and one first plate in the second configuration;

the housing combines one image plate, one base plate, and one second plate in the third configuration; and the housing combines one image plate, one base plate, one first plate, and one third plate in the fourth configuration.

7. A phantom assembly as recited in claim 1, further comprising:
   a first housing containing one image plate and one base plate;
   a second housing containing one first plate;
   a third housing containing one second plate; and
   a fourth housing containing one third plate.

8. A phantom assembly as recited in claim 7, in which the phantom assembly operates in:
   a first configuration in which the first housing is detached from the first, second, and third housings;
   a second configuration in which the second housing is detachably attached to the first housing;
   a third configuration in which the third housing is detachably attached to the first housing; and
   a fourth configuration in which the first and third housings are detachably attached to the first housing.

9. A phantom assembly as recited in claim 7, in which the first, second, third, and fourth housings are keyed to allow the first, second, third, and fourth housings to be detachably attached only in the first, second, third, and fourth configurations.

10. A phantom assembly as recited in claim 7, in which key slots are formed in the first, second, third, and fourth housings such that the first, second, third, and fourth housings may be detachably attached only in the first, second, third, and fourth configurations.

11. A phantom assembly as recited in claim 7, in which key projections are formed in the first, second, third, and fourth housings such that the first, second, third, and fourth housings may be detachably attached only in the first, second, third, and fourth configurations.

12. A phantom assembly as recited in claim 1, further comprising:
   a first housing containing one image plate and one base plate;
   a second housing containing one image plate, one base plate, and one first plate;
   a third housing containing one image plate, one base plate, and one second plate; and
   a fourth housing containing one image plate, one base plate, one first plate, and one third plate.

13. A method of testing x-ray equipment comprising:
   providing at least one image plate made of at least one image plate material;
   forming at least one base plate by selecting, sizing, and dimensioning at least one base plate material such that one base plate, in combination with one image plate, yields a first transmitted energy spectrum that emulates a first reference energy spectrum associated with a human chest;
   forming at least one first plate by selecting, sizing, and dimensioning at least one first plate material such that one first plate, in combination with one image plate and one base plate, yields a second transmitted energy spectrum that emulates a second reference energy spectrum associated with a human abdomen;
   forming at least one second plate by selecting, sizing, and dimensioning at least one second plate material such that one second plate, in combination with one image plate and one base plate, yields a first transmitted doserate that emulates a first reference doserate associated with a human chest; and
   forming at least one third plate by selecting, sizing, and dimensioning at least one third plate material such that one third plate, in combination with one image plate, one base plate, and one first plate yields a second transmitted doserate that emulates a second reference doserate associated with a human abdomen; and
   testing the x-ray equipment using at least one of the at least one image plate, the at least one base plate, at least one first plate, the at least one second plate, and the at least one third plate.

14. A method as recited in claim 13, further comprising the step of providing a housing defining a first slot adapted to receive the first plate and a second slot defining a first portion sized and dimensioned to receive the second plate and a second portion sized and dimensioned to receive the third plate.

15. A method as recited in claim 14, in which the at least one second plate, the at least one third plate, and second slot are sized and dimensioned such that the second slot receives only one of the first and second plates at a time.

16. A method as recited in claim 13, further comprising the steps of:
   combining one image plate and one base plate in a first configuration;
   combining one image plate, one base plate, and one first plate in a second configuration;
   combining one image plate, one base plate, and one second plate in a third configuration; and
   combining one image plate, one base plate, one first plate, and one third plate in a fourth configuration.

17. A phantom assembly for testing x-ray equipment comprising:
   a base assembly comprising
      a base housing,
      an image plate made of at least one image plate material,
      at least one base plate made of at least one base material, and
      a base mounting portion;
   a first plate assembly comprising
      a first plate housing,
      a first plate made of at least one first plate material,
      a primary second housing mounting portion, and
      a secondary second housing mounting portion;
   a second plate assembly comprising
      a second plate housing,
      a second plate made of at least one second plate material, and
      a third housing mounting portion;
   a third plate assembly comprising
      a third plate housing,
      a third plate made of at least one third plate material,
      a fourth housing mounting portion; wherein
   the at least one base material is selected, sized, and dimensioned such that the base plate, in combination with the image plate, yields a first transmitted energy spectrum that emulates a first reference energy spectrum associated with a human chest;
   the at least one first plate material is selected, sized, and dimensioned such that the first plate, in combination with the image plate and the base plate, yields a second transmitted energy spectrum that emulates a second reference energy spectrum associated with a human abdomen;

the at least one second plate material is selected, sized, and dimensioned such that the second plate, in combination with the image plate and the base plate, yields a first transmitted doserate that emulates a first reference doserate associated with a human chest;

the at least one third plate material is selected, sized, and dimensioned such that the third plate, in combination with the image plate, the base plate, and the first plate yields a second transmitted doserate that emulates a second reference doserate associated with a human abdomen;

the base mounting portion and the primary second housing mounting portion are configured to allow the first plate housing to be detachably attached to the base housing;

the secondary second housing mounting portion and the third housing mounting portion are configured to allow the second plate housing to be detachably attached to the base housing; and the base mounting portion and the fourth housing mounting portion are configured to allow the third plate housing to be detachably attached to the base housing.

18. A phantom assembly as recited in claim 17, in which the base mounting portion, the primary second housing mounting portion, the secondary second housing mounting portion, the third housing mounting portion, and the fourth housing mounting portion are keyed such that the phantom assembly operates only in:

a first configuration in which the first housing is detached from the first, second, and third housings;

a second configuration in which the second housing is detachably attached to the first housing;

a third configuration in which the third housing is detachably attached to the first housing; and a fourth configuration in which the first and third housings are detachably attached to the first housing.

19. A phantom assembly as recited in claim 17, in which:

the base mounting portion comprises a first key slot;

the primary second housing mounting portion defines a first key projection, where the first key slot is configured to slidingly receive the first key projection;

the secondary second housing mounting portion defines a second key slot;

the third housing mounting portion defines a second key projection, where the first key slot is configured to slidingly receive the second key projection; and the fourth housing mounting portion defines a third key projection, where the first key slot is configured to slidingly receive the third key projection.

20. A phantom assembly as recited in claim 17, in which:

the base mounting portion comprises a first set of key openings;

the primary second housing mounting portion defines a first set of key projections, where the first set of key openings is configured to receive the first set of key projections;

the secondary second housing mounting portion defines a second set of key openings;

the third housing mounting portion defines a second set of key projections, where the first set of key openings is configured to receive the second set of key projections; and the fourth housing mounting portion defines a third set of key projections, where the second set of key openings is configured to receive the third set of key projections.

* * * * *